United States Patent
Portal

(10) Patent No.: US 8,394,990 B2
(45) Date of Patent: Mar. 12, 2013

(54) PHENYLUREA INHIBITORS OF THE ENZYME SOAT-1 AND PHARMACEUTICAL/COSMETIC COMPOSITIONS COMPRISED THEREOF

(75) Inventor: Thibaud Portal, Opio (FR)

(73) Assignee: Galderma Research & Development, Biot (FR)

( * ) Notice: Subject to any disclaimer, the term of this patent is extended or adjusted under 35 U.S.C. 154(b) by 283 days.

(21) Appl. No.: 12/717,984

(22) Filed: Mar. 5, 2010

(65) Prior Publication Data

US 2010/0197735 A1 Aug. 5, 2010

Related U.S. Application Data

(63) Continuation of application No. PCT/EP2008/061769, filed on Sep. 5, 2008.

(60) Provisional application No. 60/960,094, filed on Sep. 14, 2007.

(30) Foreign Application Priority Data

Sep. 6, 2007 (FR) ...................... 07 57392

(51) Int. Cl.
C07C 273/00 (2006.01)
A61K 31/445 (2006.01)
(52) U.S. Cl. .......................... 564/47; 514/329
(58) Field of Classification Search ........................ None
See application file for complete search history.

(56) References Cited

U.S. PATENT DOCUMENTS

2004/0038987 A1 2/2004 Shibuya et al.

OTHER PUBLICATIONS

Vippagunta, S. et al., Adv. Drug Deliv. Rev. 2001, vol. 48, pp. 3-26.*
O'Brien et al., "Inhibitors of Acyl-CoA:Cholesterol O-Acyl Transferase (ACAT) as Hypocholesterolemic Agents. Incorporation of Amide or Amine Functionalities into a Series of Disubstituted Ureas and Carbamates. Effects on ACAT Inhibition in Vitro and Efficacy in Vivo." J. Med. Chem., 1994, pp. 1810-1822, vol. 37, No. 12, American Chemical Society, WDC.

* cited by examiner

*Primary Examiner* — David K O'Dell
*Assistant Examiner* — Heidi Reese
(74) *Attorney, Agent, or Firm* — SNR Denton US LLP

(57) ABSTRACT

Phenylurea compounds of formula (I):

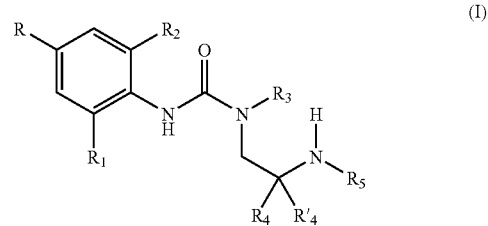

are inhibitors of the enzyme SOAT-1. Cosmetic and pharmaceutical compositions containing them are useful for treating various disorders, such as acne, or have cosmetic applications. An exemplary species is 1-[1-(biphenyl-2-ylamino)cyclopentylmethyl]-3-(2,6-diisopropylpheny)urea.

20 Claims, No Drawings

PHENYLUREA INHIBITORS OF THE ENZYME SOAT-1 AND PHARMACEUTICAL/COSMETIC COMPOSITIONS COMPRISED THEREOF

CROSS-REFERENCE TO EARLIER APPLICATIONS

This application is a continuation of PCT/EP 2008/061769, filed Sep. 5, 2008 and designating the United States (published in the English language on Mar. 12, 2009 as WO 2009/030746 A1), which claims foreign priority under 35 U.S.C. §119 of FR 0757392, filed in France on Sep. 6, 2007 and also claims benefit under 35 U.S.C. §119(e) of U.S. Provisional Application No. 60/960,094, filed Sep. 14, 2007, each hereby expressly incorporated by reference in its entirety and each assigned to the assignee hereof.

BACKGROUND OF THE INVENTION

1. Technical Field of the Invention

The present invention relates to novel phenylurea compound inhibitors of the enzyme SOAT-1 (from "Sterol-O-Acyl Transferase-1", also named ACAT-1 from "Acylcoenzyme A Cholesterol Acyl Transferase"). It also relates to their formulation into pharmaceutical compositions useful in human or veterinary medicine or else into cosmetic compositions and also their non-therapeutic applications.

2. Description of Background and/or Related and/or Prior Art

Compounds having an SOAT-1 inhibitory type of activity are widely described in the literature as having effects in the regulation of biological processes involving cholesterol and derivatives thereof. These properties confer on this class of compounds a marked potential in the treatment or prevention of many diseases and more particularly in dermatology and in cardiovascular diseases or disorders of the central nervous system. Most of the biological effects of the SOAT-1 inhibitors are mediated by the prevention of the synthesis of esters of cholesterol by the enzyme SOAT-1. Among the documents of the prior art describing molecules inhibiting SOAT-1, exemplary are WO 96/10559, EP-0370740, EP-0424194, U.S. Pat. No. 4,623,663, EP-0557171, U.S. Pat. No. 5,003,106, EP-0293880, EP-0433662 and U.S. Pat. No. 5,106,873, which describe compounds for treating arteriosclerosis or hypercholesterolaemia. The therapeutic potential of the SOAT-1 inhibitors in the treatment of cardiovascular diseases and in particular of hypercholesterolaemia and arteriosclerosis is also described in Kharbanda R. K. et al., in *Circulation*. 2005, 11, 804. The potential of the SOAT-1 inhibitors for the treatment of Alzheimer's disease has also been reported in the literature, for example by Puglielli, L. et al., in *Nature Neurosciences* 2003, 6 (4), 345.

For their part, U.S. Pat. Nos. 6,133,326, 6,271,268 and WO 2005/034931 describe compounds inhibiting SOAT-1 for inhibiting the production of sebum. In the field of dermatology in particular, it is particularly advantageous to prevent the excessive production of sebum and all the associated conditions.

Sebum is produced by the sebaceous gland. The greatest concentration of sebaceous glands is located on the face, the shoulders, the back and the scalp. The sebum is secreted at the surface of the skin, where it has a major physiological role, associated with the maintenance of the skin barrier and of a micro-environment enabling the regulation of the cutaneous bacterial and fungal flora.

Hyperproduction of sebum is most commonly associated with a skin or scalp of greasy appearance, which is the cause of discomfort and a poor appearance. Moreover, the hyperproduction of sebum can cause seborrhoeic dermatitis and is associated with increased incidence or severity of acne. The esters of cholesterol produced in the sebaceous gland by SOAT-1 are one of the components of the sebum, among several classes of lipids including the triglycerides, esters of waxes and the squalenes, as described by Nikkari, T., in *J Invest Derm* 1974, 62, 257. The inhibition of this enzyme or of other acyltransferases can thus make it possible to inhibit the production of sebum. U.S. Pat. No. 6,133,326, in particular, describes the inhibition of sebum by inhibitors of ACAT-1 (also called SOAT-1). Nonetheless, at present no treatment utilizing such inhibitors is available on the market. The only treatments to remedy or alleviate disorders linked with hyperseborrhoea are systemic hormonal treatments or systemic treatment with 13-cis retinoic acid, treatments whose side effects considerably restrict their field of application. There is thus a clear medical and cosmetic need for the treatment of disorders and pathologies linked to the hyperproduction of sebum.

SUMMARY OF THE INVENTION

The present invention features novel phenylurea compounds which display, in particular by comparison with the compounds of the closest structures described in U.S. Pat. No. 5,106,873, better inhibition of the enzyme SOAT-1.

Thus, this invention features novel phenylurea compounds, inhibitors of the enzyme SOAT-1, having the following general formula (I):

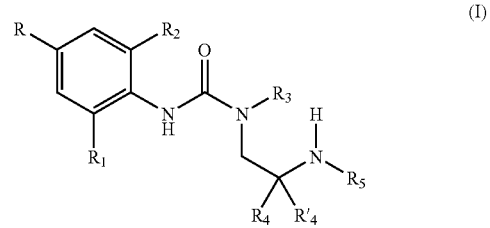

wherein,

R is a hydrogen atom, a ($C_1$-$C_6$) alkyl radical, a —$CH_2$—$NR_6R_7$ radical, a —C(O)—$NR_6R_7$ radical, or a —C(S)$NR_6R_7$ radical, in which $R_6$ is a hydrogen atom or a ($C_1$-$C_4$) alkyl radical and $R_7$ is a hydrogen atom, a phenyl or a cycloalkyl radical, $R_1$ is a hydrogen atom, a ($C_1$-$C_6$) alkyl radical or a chlorine, bromine or fluorine atom, $R_2$ is a ($C_1$-$C_6$) alkyl radical, $R_3$ is a hydrogen atom or a ($C_1$-$C_6$) alkyl radical, $R_4$ and $R'_4$ are identical and are each a ($C_1$-$C_6$) alkyl radical or else $R_4$ and $R'_4$ are linked together and form, with the carbon atom from which they depend, a cycloalkyl group, an indanyl group, or a saturated heterocyclic group selected from the piperidine, tetrahydropyran, pyrrolidine, tetrahydrothiophene, tetrahydrofuran and azetidine groups, the piperidine, pyrrolidine and azetidine being optionally substituted on the nitrogen atom by an $R_8$, —C(O)$R_8$ or —$SO_2R_8$ radical, with $R_8$ representing a ($C_1$-$C_4$) alkyl radical, $R_5$ is a phenyl radical ortho, meta or para monosubstituted with an iodine atom or with a phenyl, 2-pyridyl, 3-pyridyl or 4-pyridyl radical, and pharmaceutically acceptable salts, solvates or hydrates thereof.

"Alkyl radical" means a linear or branched, saturated hydrocarbon chain. "($C_1$-$C_6$) alkyl radical" means an alkyl chain having from 1 to 6 carbon atoms. Representative of ($C_1$-$C_6$) alkyl radicals, methyl, ethyl, n-propyl, iso-propyl, n-butyl, t-butyl, sec-butyl, pentyl and hexyl radicals are exemplary. "($C_1$-$C_4$) alkyl radical" means an alkyl chain having from 1 to 4 carbon atoms. Representative of ($C_1$-$C_4$) alkyl radicals, the methyl, ethyl, n-propyl, iso-propyl, n-butyl, t-butyl and sec-butyl groups are exemplary.

"Cycloalkyl radical" designates a cyclic, saturated hydrocarbon chain having from 3 to 7 carbon atoms. Representative of cycloalkyl radicals, the cyclopropyl, cyclobutyl, cyclopentyl, cyclohexyl and cycloheptyl radicals are exemplary.

DETAILED DESCRIPTION OF BEST MODE AND SPECIFIC/PREFERRED EMBODIMENTS OF THE INVENTION

Preferred are the compounds of formula (I) defined above, wherein:

R is a hydrogen atom, $R_1$ is a methyl, ethyl, isopropyl or t-butyl radical, $R_2$ is a methyl, ethyl, isopropyl or t-butyl radical, $R_3$ is a hydrogen atom, $R_4$ and $R'_4$ are identical and are each an ethyl radical or else $R_4$ and $R'_4$ are linked together and form, with the carbon atom from which they depend, either a cyclopentyl, cyclohexyl, cycloheptyl or indanyl group, or a tetrahydropyran or piperidine group, or piperidine substituted on the nitrogen atom by an $R_8$, —C(O)$R_8$ or —SO$_2$$R_8$ radical, with $R_8$ representing a ($C_1$-$C_4$) alkyl radical, $R_5$ is an o-, m- or p-biphenyl, o-, m- or p-iodophenyl, o-, m- or p-(2-pyridyl)phenyl, o-, m- or p-(3-pyridyl)phenyl or else o-, m- or p-(4-pyridyl)phenyl radical, and pharmaceutically acceptable salts, solvates or hydrates thereof.

According to the present invention, among the compounds of formula (I) as defined above, those which display one or a combination of the following characteristics, when they do not exclude one another, are more particularly preferred:

R is a hydrogen atom, $R_1$ is an ethyl, isopropyl, or t-butyl radical, $R_2$ is a methyl, ethyl or isopropyl radical, $R_3$ is a hydrogen atom, $R_4$ and $R'_4$ are identical and are each an ethyl radical, or else $R_4$ and $R'_4$ are linked together and form, with the carbon atom for which they depend, either a cyclopentyl or cyclohexyl group, or a tetrahydropyran or piperidine group, or piperidine substituted on the nitrogen atom with a methyl, ethyl, —C(O)CH$_3$ or —SO$_2$CH$_3$ radical, and $R_5$ is an o- or p-biphenyl, o- or p-iodophenyl, o- or p-(2-pyridyl)phenyl, o- or p-(3-pyridyl)phenyl or o- or p-(4-pyridyl)phenyl radical.

The compounds of formula (I) below, and pharmaceutically acceptable salts, solvates or hydrates thereof, are particularly preferred:

1-(2,6-diisopropylphenyl)-3-[1-(4-iodophenylamino)-cyclopentylmethyl]-urea, compound (I.1) with R=H, $R_1$=$R_2$=iPr; $R_3$=H; $R_4$ and $R'_4$ are linked together to form a cyclopentyl; $R_5$=p-I-Ph.

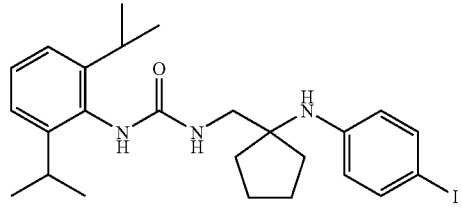

(I.1)

1-(2,6-diisopropylphenyl)-3-[1-(2-iodophenylamino)-cyclopentylmethyl)-urea, compound (I.2) with R=H, $R_1$=$R_2$=iPr; $R_3$=H; $R_4$ and $R'_4$ are linked together to form a cyclopentyl; $R_5$=o-I-Ph

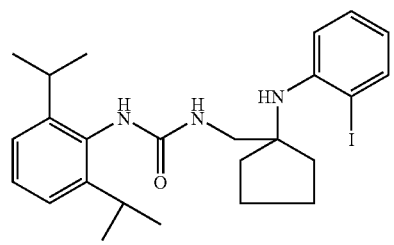

(I.2)

1-[1-(biphenyl-4-ylamino)-cyclopentylmethyl]-3-(2,6-diisopropylphenyl)-urea, compound (I.3) with R=H, $R_1$=$R_2$=iPr; $R_3$=H; $R_4$ and $R'_4$ are linked together to form a cyclopentyl; $R_5$=p-BiPh.

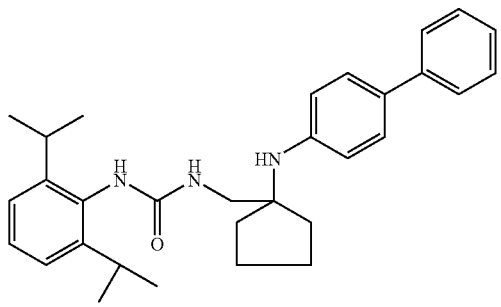

(I.3)

1-[1-(biphenyl-2-ylamino)-cyclopentylmethyl]-3-(2,6-diisopropylphenyl)-urea, compound (I.4) with R=H, $R_1$=$R_2$=iPr; $R_3$=H; $R_4$ and $R'_4$ are linked together to form a cyclopentyl; $R_5$=o-BiPh.

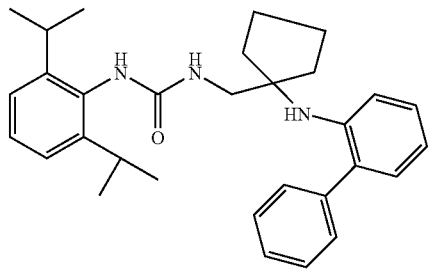

(I.4)

1-[1-(biphenyl-2-ylamino)-cyclopentylmethyl]-3-(2,6-diethylphenyl)-urea, compound (I.5) with R=H, $R_1$=$R_2$=Et; $R_3$=H; $R_4$ and $R'_4$ are linked together to form a cyclopentyl; $R_5$=o-BiPh.

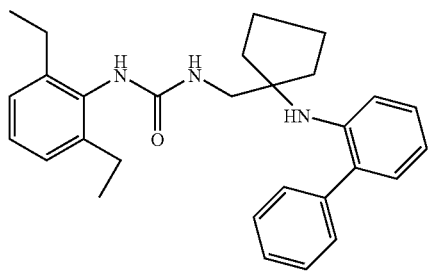
(I.5)

1-[1-(biphenyl-2-ylamino)-cyclohexylmethyl]-3-(2,6-diisopropylphenyl)-urea, compound (I.6) with R=H, $R_1$=$R_2$=iPr; $R_3$=H; $R_4$ and $R'_4$ are linked together to form a cyclohexyl; $R_5$=o-BiPh

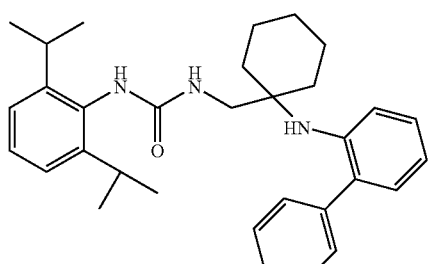
(I.6)

1-[1-(biphenyl-2-ylamino)-cyclopentylmethyl]-3-(2-tert-butyl-6-methylphenyl)-urea, compound (I.7) with R=H, $R_1$=tBu; $R_2$=Me; $R_3$=H; $R_4$ and $R'_4$ are linked together to form a cyclopentyl; $R_5$=o-BiPh.

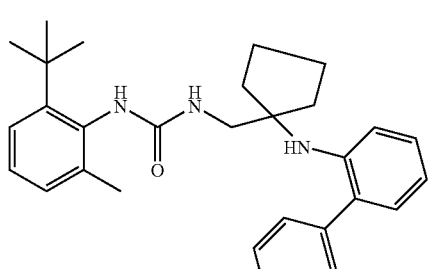
(I.7)

1-(2,6-diisopropylphenyl)-3-[1-(2-pyridin-2-yl-phenylamino)-cyclopentylmethyl]-urea, compound (I.8) with R=H, $R_1$=$R_2$=iPr; $R_3$=H; $R_4$ and $R'_4$ are linked together to form a cyclopentyl; $R_5$=2-(2-pyridinyl)-phenyl.

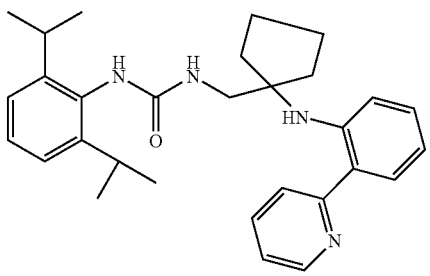
(I.8)

1-(2,6-diisopropylphenyl)-3-[1-(2-pyridin-4-yl-phenylamino)-cyclopentylmethyl]-urea, compound (I.9) with R=H, $R_1$=$R_2$=iPr; $R_3$=H; $R_4$ and $R'_4$ are linked together to form a cyclopentyl; $R_5$=2-(4-pyridinyl)-phenyl.

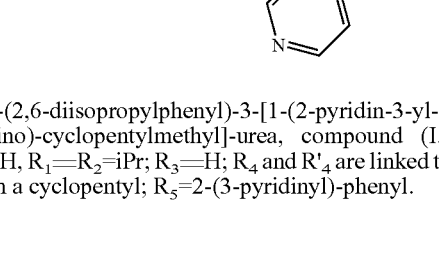
(I.9)

1-(2,6-diisopropylphenyl)-3-[1-(2-pyridin-3-yl-phenylamino)-cyclopentylmethyl]-urea, compound (I.10) with R=H, $R_1$=$R_2$=iPr; $R_3$=H; $R_4$ and $R'_4$ are linked together to form a cyclopentyl; $R_5$=2-(3-pyridinyl)-phenyl.

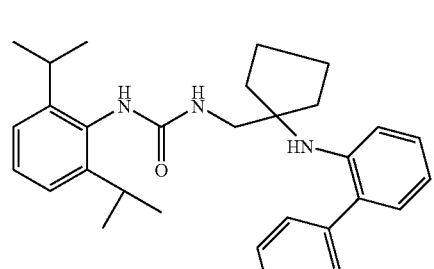
(I.10)

1-(2,6-diisopropyl-phenyl)-3-[1-(2-pyridin-4-yl-phenylamino)-cyclohexylmethyl]urea, compound (I.11) with R=H, $R_1$=$R_2$=iPr; $R_3$=H; $R_4$ and $R'_4$ are linked together to form a cyclohexyl; $R_5$=2-(4-pyridinyl)-phenyl.

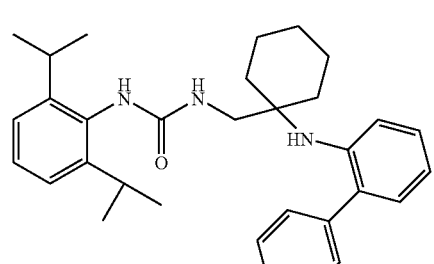
(I.11)

1-(2,6-diisopropylphenyl-3-[1-(2-pyridin-3-yl-phenylamino)-cyclohexylmethyl]-urea, compound (I.12) with R═H, R$_1$═R$_2$=iPr; R$_3$═H; R$_4$ and R'$_4$ are linked together to form a cyclohexyl; R$_5$=2-(3-pyridinyl)-phenyl.

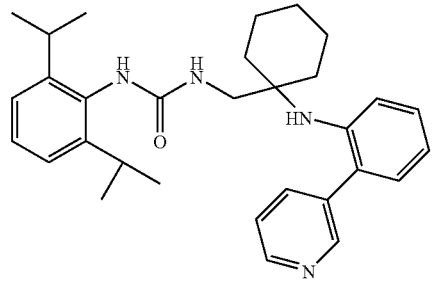

(I.11)

1-(2,6-diisopropylphenyl)-3-[1-(2-pyridin-2-yl-phenylamino)-cyclohexylmethyl]-urea, compound (I.13) with R═H, R$_1$═R$_2$=iPr; R$_3$═H; R$_4$ and R'$_4$ are linked together to form a cyclohexyl; R$_5$=2-(2-pyridinyl)-phenyl.

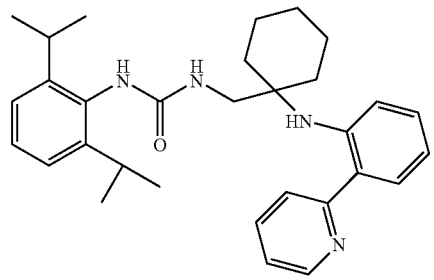

(I.13)

1-(2,6-diisopropylphenyl)-3-[1-(4-pyridin-2-yl-phenylamino)-cyclopentylmethyl]-urea, compound (I.14) with R═H, R$_1$═R$_2$=iPr; R$_3$═H; R$_4$ and R'$_4$ are linked together to form a cyclopentyl; R$_5$=4-(2-pyridinyl)-phenyl.

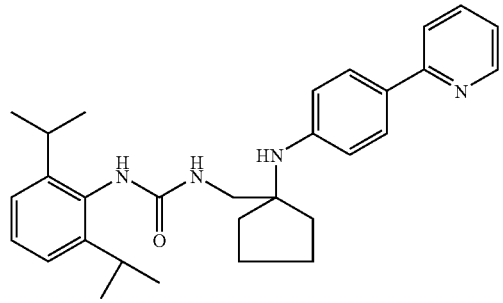

(I.14)

1-(2,6-diisopropylphenyl)-3-[1-(4-pyridin-4-yl-phenylamino)-cyclopentylmethyl]-urea, compound (I.15) with R═H, R$_1$═R$_2$=iPr; R$_3$═H; R$_4$ and R'$_4$ are linked together to form a cyclopentyl; R$_5$=4-(4-pyridinyl)-phenyl.

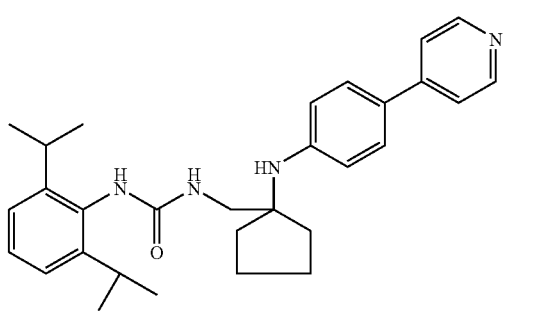

(I.15)

1-(2,6-diisopropylphenyl)-3-[1-(4-pyridin-3-yl-phenylamino)-cyclopentylmethyl]-urea, compound (I.16) with R═H, R$_1$═R$_2$=iPr; R$_3$═H; R$_4$ and R'$_4$ are linked together to form a cyclopentyl; R$_5$=4-(3-pyridinyl)-phenyl.

(I.16)

1-[4-(biphenyl-2-ylamino)-piperidin-4-ylmethyl]-3-(2,6-diisopropylphenyl)-urea, compound (I.17) with R═H, R$_1$═R$_2$=iPr; R$_3$═H; R$_4$ and R'$_4$ are linked together to form a piperidine; R$_5$=o-BiPh.

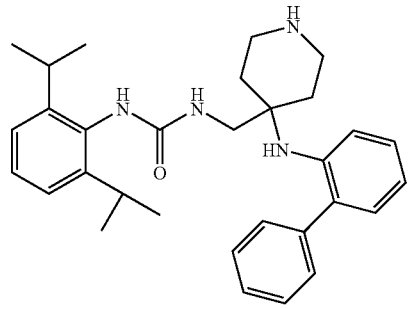

(I.17)

1-[4-(biphenyl-2-ylamino)-1-methylpiperidin-4-yl-methyl]-3-(2,6-diisopropylphenyl)-urea, compound (I.18) with R═H, R$_1$═R$_2$=iPr; R$_3$═H; R$_4$ and R'$_4$ are linked together to form an N-Me-piperidine; R$_5$=o-BiPh

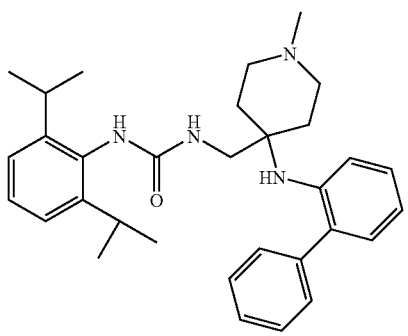

1-[1-acetyl-4-(biphenyl-2-ylamino)-piperidin-4-yl-methyl]-3-(2,6-diisopropylphenyl)-urea, compound (I.19) with R═H, R$_1$═R$_2$═iPr; R$_3$═H; R$_4$ and R'$_4$ are linked together to form an N-Ac-piperidine; R$_5$=o-BiPh.

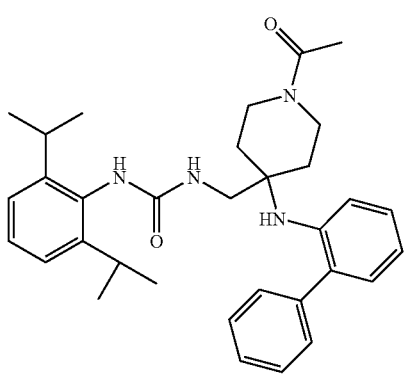

1-[4-(biphenyl-2-ylamino)-1-methanesulfonyl-piperidin-4-yl-methyl]-3-(2,6-diisopropylphenyl)-urea, compound (I.20) with R═H, R$_1$═R$_2$═iPr; R$_3$═H; R$_4$ and R'$_4$ are linked together to form an N-methylsulfonyl-piperidine; R$_5$=oBiPh

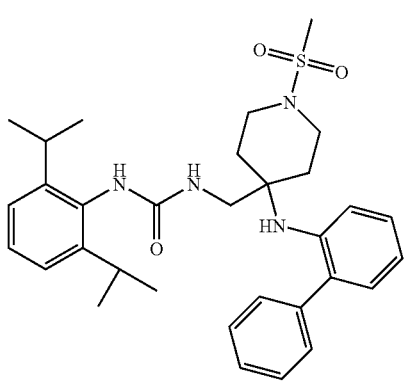

1-[4-(biphenyl-2-ylamino)-1-ethyl-piperidin-4-yl-methyl]-3-(2,6-diisopropylphenyl)-urea, compound (I.21) with R═H, R$_1$═R$_2$═iPr; R$_3$═H; R$_4$ and R'$_4$ are linked together to form an N-ethyl-piperidine; R$_5$=o-BiPh

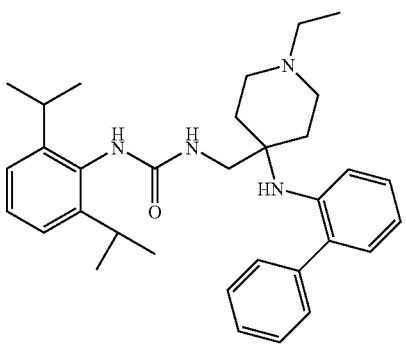

1-[4-(biphenyl-2-ylamino)-tetrahydropyran-4-ylmethyl]-3-(2,6-diisopropylphenyl)-urea, compound (I.22) with R═H, R$_1$═R$_2$═iPr; R$_3$═H; R$_4$ and R'$_4$ are linked together to form a tetrahydropyran; R$_5$=o-BiPh

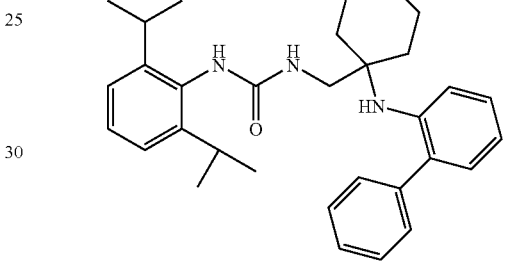

The salts of the compounds according to the invention are prepared according to techniques well known to one skilled in the art. The salts of the compounds of formula (I) according to the present invention include those with mineral or organic acids which enable a convenient separation or crystallization of the compounds of formula (I), and of the pharmaceutically acceptable salts. As appropriate acids, picric acid, oxalic acid or an optically active acid, for example a tartaric acid, a dibenzoyltartaric acid, a mandelic acid or a camphorsulfonic acid, and those which form physiologically acceptable salts, such as the hydrochloride, the hydrobromide, the sulfate, the hydrogen sulfate, the dihydrogen phosphate, the maleate, the fumarate, the 2-naphthalenesulfonate and the paratoluene-sulfonate can be cited, the hydro-chloride being preferred.

The solvates or hydrates can be obtained directly from the synthetic process, the compound (I) being isolated in the form of a hydrate, for example a mono- or hemi-hydrate or a solvate of a reaction or purification solvent.

The compounds of formula (I) can be purified by any standard purification technique, for example by crystallization or purification by column chromatography.

When a compound of formula (I) according to the invention exhibits one or more asymmetric carbons, the optical isomers of that compound are an integral part of the present invention. The compounds of formula (I) can thus be in the form of a pure isomer or of a mixture of isomers in any proportion.

The compounds of formula (I) according to the invention can be prepared according to SCHEME 1 below, wherein R, R$_1$, R$_2$, R$_3$, R$_4$ and R'$_4$ are as defined for the compounds of formula (I) and R'$_5$ is the group R$_5$ or a precursor group of R$_5$:

SCHEME 1:

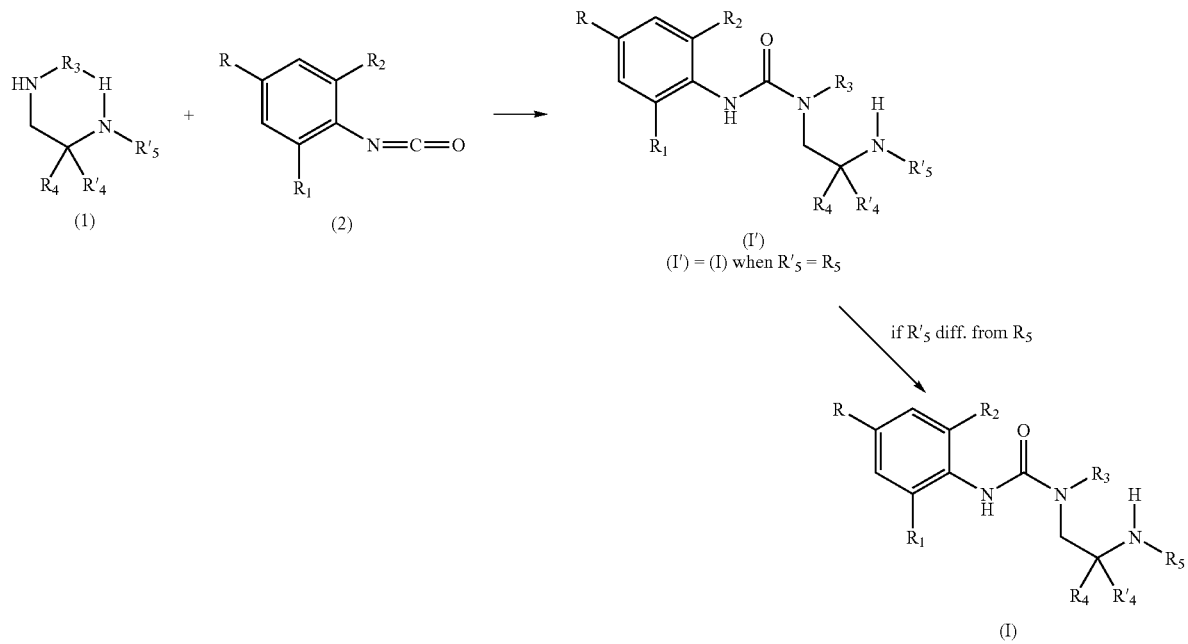

The compounds of general formula (I) can be prepared by addition of the primary or secondary amines of general formula (1) to the corresponding urea precursors, for example the isocyanates (2), in accordance for example with the reactions described by O'Brien, P. M. et al. in *J Med Chem.*, 1994, 37 (12), 1810-1822. The compounds of formula (1) can directly contain the group $R_5=R'_5$ of the final desired compound of formula (I) and in that case the compound (I') corresponds to the desired compound (I); this is for example the case when $R_5$=o, m, or p-iodophenyl. In certain cases, the addition can be effected with a compound of formula (1) containing a precursor group $R'_5$ of the group $R_5$, to form an intermediate compound (I') which will then have to be transformed to obtain the desired group $R_5$. For example in the case of the preparation of the compounds of formula (I) wherein $R_5$=o, m, or p-biphenyl or else any isomers of phenylpyridine, the compound of formula (1) utilized contains a group $R'_5$=o, m, or p-iodo-phenyl, the iodine being in the position corresponding to the desired phenyl or pyridyl group. The compound of formula (I') which corresponds to the compound of formula (I) wherein $R'_5$=o, m, or p-iodo-phenyl is formed as an intermediate, and is then subjected to a coupling reaction of the Suzuki type or paired with a phenylboronic acid partner or corresponding pyridylboronic acid, according to the standard conditions described for example in Suzuki et al., *Synth. Commun.*, 1981, 11, 513 or Sharp, M. J. *Tet Lett.*, 1985, 26, 5997) or else the optimized conditions if necessary (see for example Littke, A. F. et al., *J Am Chem. Soc.*, 2000, 122 (17), 4020-4028).

The primary amines of general formula (1) wherein $R_3$=H can be prepared according to the following SCHEME 2, wherein $R_4$ and $R'_4$ are as defined for the compounds of formula (I) and $R'_5$ is the group $R_5$ or a precursor group of $R_5$:

SCHEME 2:

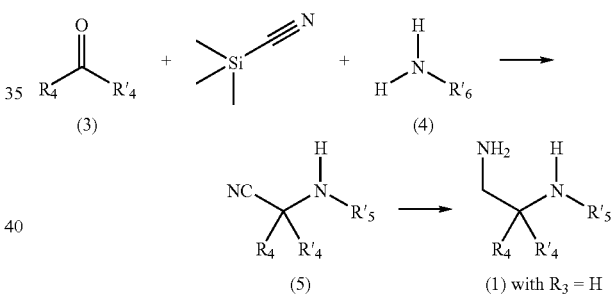

The ketones of formula (3) are first reacted with the anilines of formula (4) in the presence of trimethylsilane cyanide, to give the nitrile compounds of formula (5), in accordance for example with the conditions described in Matsumoto, K. et al., *Helv Chim Acta* 2005, 88 (7), 1734-1753 or Nieto, M. J. et al., *J Comb Chem.*, 2005, 7(2), 258-263. The reduction of the nitrile function of the compound (5) can then be effected, for example by reaction with a hydride as described in Whelan, B. et al., *Synthesis* 1994, (8), 832-836, resulting in the corresponding primary amines of formula (1).

The isocyanates of formula (2) are commercial compounds or are prepared according to techniques well known to one skilled in the art.

The functional groups possibly present in the reaction intermediates used in the process can be protected, either in permanent form, or in temporary form, by protective groups which ensure an unambiguous synthesis of the expected compounds. The protection and deprotection reactions are effected by techniques well known to the person skilled in the art. Temporary protective groups of amines, alcohols or carboxylic acids are understood to mean protective groups such as those described in "Protective Groups in Organic Chemistry", Ed. McOmie J. W.

F., Plenum Press, 1973, in "Protective Groups in Organic Synthesis", 2nd edition, Greene T. W. and Wuts P. G. M., Ed. John Wiley and Sons, 1991 and in "Protecting Groups", Kocienski P. J., 1994, Georg Thieme Verlag.

The compounds (I) according to the invention, and the pharmaceutically acceptable salts, solvates and/or hydrates thereof, have inhibitory properties towards the enzyme SOAT-1. This inhibitory action on the enzyme SOAT-1 is measured according to a primary enzymatic test HepG2, as described below. The preferred compounds according to the present invention exhibit a concentration enabling 50% inhibition of the response of the enzyme ($IC_{50}$) less than or equal to 1000 nM, preferably less than or equal to 500 nM and advantageously less than or equal to 100 nM.

The present invention also features medicaments comprising the compounds of formula (I) as described above, and the pharmaceutically acceptable salts, pharmaceutically acceptable solvates and/or hydrates thereof.

The present invention also features formulating at least one compound of formula (I), and the salts, pharmaceutically acceptable solvates and/or hydrates thereof, into medicaments to prevent and/or treat disorders of the sebaceous gland such as hyperseborrhoea, acne, seborrhoeic dermatitis, atopic dermatitis or rosacea, ocular diseases such as ocular rosacea, disorders of the meibomian gland, such as blepharitis, meibomitis, chalazion, dry eye, conjunctivitis or keratoconjunctivitis, or else diseases such as hypercholesterolaemia, arterio-sclerosis or Alzheimer's disease. The compounds according to the invention are particularly suitable for formulation into pharmaceutical compositions useful for the treatment of acne. The compounds according to the invention are thus suitable for utilization in the treatment of the pathologies listed above.

The present invention also features pharmaceutical or cosmetic compositions containing, formulated into a physiologically acceptable carrier, at least one compound of formula (I) as defined above, or one of the salts, pharmaceutically acceptable solvates and/or hydrates thereof. The compositions according to the invention thus contain a physiologically acceptable carrier or at least one physiologically or pharmaceutically acceptable excipient, selected on the basis of the desired cosmetic or pharmaceutical form and the selected mode of administration, whether regime or regimen.

Physiologically acceptable carrier or medium means a carrier compatible with the skin, the mucous membranes and/or the integuments.

The administration of the compositions according to the invention can be effected by the enteral, parenteral, rectal, topical or ocular route, whether regime or regimen. Preferably, the pharmaceutical composition is in a form suitable for application by the topical route.

For the enteral route, the composition, more particularly the pharmaceutical composition, can be in the form of tablets, gel capsules, sugar-coated tablets, syrups, suspensions, solutions, powders, granules, emulsions, microspheres or nanospheres or lipid or polymeric vesicles enabling a controlled release. For the parenteral route, the composition can be in the form of solutions for perfusion or for injection.

The compositions according to the invention contain a compound according to the invention, in a quantity sufficient to elicit the desired, cosmetic, prophylactic or therapeutic effect. The compounds according to the invention are generally administered at a daily dose of about 0.001 mg/kg to 100 mg/kg body weight, in one to three doses. The compounds are administered by the systemic route at a concentration generally ranging from 0.001 to 10% by weight, preferably from 0.01 to 2% by weight, relative to the weight of the composition.

For the topical route, the pharmaceutical composition according to the invention is more particularly useful for the treatment of the skin and the mucous membranes and can be in the form of ointments, creams, milks, pomades, powders, impregnated tampons, syndets, solutions, gels, sprays, foams, suspensions, lotions, sticks, shampoo, or cleansing bases. They can also be in the form of suspensions of microspheres or nanospheres or lipid or polymeric vesicles or polymeric patches and hydrogels enabling a controlled release. This composition for the topical route can be in anhydrous form, in aqueous form or in the form of an emulsion.

The compounds are utilized by the topical route at a concentration generally ranging from 0.001 to 10% by weight, preferably from 0.01 to 2% by weight, relative to the total weight of the composition.

The compounds of formula (I) according to the invention, and the salts, pharmaceutically acceptable solvates and/or hydrates thereof also are useful in the cosmetic field, in particular in body and hair hygiene and more particularly to combat or prevent greasy skin, greasy hair or greasy scalp.

The present invention thus features the cosmetic utilization of a composition containing, in a physiologically acceptable carrier, at least one of the compounds of formula (I), optionally in the form of a salt, pharmaceutically acceptable solvate and/or hydrate, for body or hair hygiene.

The cosmetic compositions according to the invention containing, in a cosmetically acceptable carrier, at least one compound of formula (I) or one of the salts, pharmaceutically acceptable solvates and/or hydrates thereof, can in particular be in the form of a cream, a milk, a lotion, a gel, an ointment, a pomade, suspensions of microspheres or nanospheres or lipid or polymeric vesicles, impregnated tampons, solutions, sprays, foams, sticks, soaps, shampoos or cleansing bases.

The concentration of compound of formula (I) in the cosmetic composition ranges from 0.001 to 3% by weight, relative to the total weight of the composition.

The pharmaceutical and cosmetic compositions as described above can also contain inert additives, or even those pharmacodynamically active as regards the pharmaceutical compositions, or combinations of these additives, and in particular:
wetting agents;
flavor improving agents;
preservatives such as esters of parahydroxybenzoic acid;
stabilizers;
moisture regulators;
pH regulators;
osmotic pressure modifiers;
emulsifying agents;
UV-A and UV-B filters;
antioxidants such as α-tocopherol, butylhydroxy-anisole or butylhydroxytoluene, super oxide dismutase, ubiquinol or certain metal chelating agents;
emollients:
moisturizing agents such as glycerol, PEG 400, thiamorpholinone and derivatives thereof or urea;
carotenoids and in particular β-carotene;
α-hydroxy acids and α-keto acids or derivatives thereof, such as lactic, malic, citric, glycolic, mandelic, tartaric, glyceric and ascorbic acids, and salts, amides or esters thereof, or β-hydroxy acids or derivatives thereof, such as salicylic acid and salts, amides or esters thereof.

Of course, one skilled in the art will take care to select any compounds to be added to these compositions in such a manner that the advantageous properties intrinsically attached to the present invention are not, or essentially not, impaired by the addition envisaged.

Furthermore, in general, the same preferences as those previously indicated for the compounds of formula (I) apply mutatis mutandis to the medicaments, cosmetic and pharmaceutical compositions and utilization of the compounds of the invention.

In order to further illustrate the present invention and the advantages thereof, the following specific examples are given, including those of biological activity, it being understood that same are intended only as illustrative and in nowise limitative. In said examples to follow, all parts and percentages are given by weight, unless otherwise indicated.

The following abbreviations are employed:
iPr=isopropyl, Ph=phenyl, p-Tolyl=4-methylphenyl, p=para, m=meta, o=ortho, BiPh=biphenyl, Me=methyl, Ac=—C(O)CH$_3$

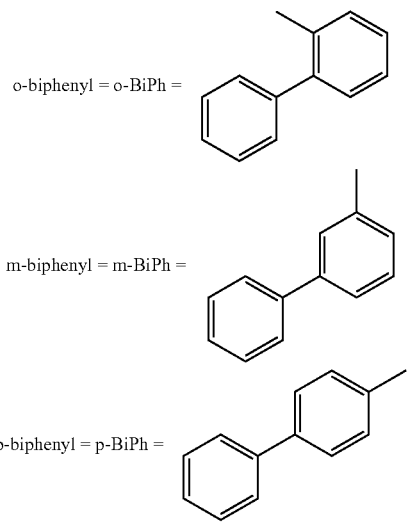

EXAMPLE 1

1-(2,6-diisopropylphenyl)-3-[1-(4-iodo-phenylamino)-cyclopentylmethyl]-urea, compound (I.1) with R=H, $R_1$=$R_2$=iPr; $R_3$=H; $R_4$ and R'$_4$ are linked together to form a cyclopentyl; $R_5$=p-I-Ph

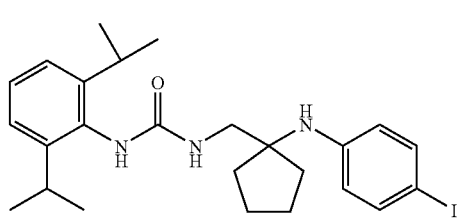

(a) Preparation of
1-(4-iodo-phenylamino)-cyclopentanecarbonitrile 3.5 g (16 mmol) of 4-iodo-aniline are added to a solution of 1.3 ml (14.7 mmol) of cyclopentanone in 20 ml of acetic acid at 0° C. The solution is stirred for 15 minutes and 2 ml (15 mmol) of trimethylsilyl cyanide are added. The reaction medium is stirred for one night at ambient temperature. It is then poured gently into a solution of ice-cooled ammonium hydroxide until the pH is basic and extracted with dichloromethane. The organic phases are combined and washed with water. They are dried over sodium sulfate. After evaporation of the solvents, 4.3 g of 1-(4-iodo-phenylamino)-cyclopentanecarbonitrile are obtained in the form of a brown oil. (Yield=94%).

(b) Preparation of
1-(4-iodophenylamino)-cyclopentanecarboxamide 4.2 g (13.4 mmol) of 1-(4-iodophenyl-amino)-cyclopentanecarbonitrile are dissolved in 40 ml of concentrated sulfuric acid. The reaction medium is stirred for 48 hrs at ambient temperature, then it is poured gently into water and the pH is adjusted to 7 with soda and [the mixture] extracted with ethyl acetate. The organic phases are combined and washed with water. They are dried over sodium sulfate. The solvents are evaporated and the residue is crystallized in a little dichloromethane and heptane. It is then filtered and dried. 4.2 g of 1-(4-iodophenylamino)-cyclopentanecarboxamide are obtained in the form of a pink solid. (M.Pt.=148° C., Yield=94%).

(c) Preparation of
(1-aminomethylcyclopentyl)-(4-iodophenyl)-amine 9.1 ml (18.2 mmol) of borane-dimethyl sulfide are added to a solution of 3 g (9.08 mmol) of 1-(4-iodo-phenylamino)-cyclopentanecarboxamide in 30 ml of THF. The reaction medium is stirred for 4 hrs at ambient temperature then for one night under reflux. It is then poured into water and extracted with ethyl acetate. The organic phases are combined and washed with water. They are dried over sodium sulfate. The solvents are evaporated. The residue is chromatographed on silica gel (ethyl acetate). 2.3 g of (1-amino-methyl-cyclopentyl)-(4-iodophenyl)-amine are obtained in the form of a pink solid. (M.Pt.=69° C., Yield=80%).

(d) Preparation of 1-(2,6-diisopropylphenyl)-3-[1-(4-iodophenylamino)-cyclopentylmethyl]-urea 800 µl (3.9 mmol) of 2,6-diisopropylphenyl isocyanate are added to a solution of 1 g (3.16 mmol) of (1-amino-methyl-cyclopentyl)-(4-iodophenyl)-amine in 50 ml of dichloromethane. The reaction medium is stirred for 1 hr at ambient temperature. The dichloromethane is evaporated and the residue is chromatographed on silica gel (pure heptane then with 20% of ethyl acetate by volume). 1.55 g of 1-(2,6-diisopropylphenyl)-3-[1-(4-iodo-phenylamino)-cyclopentylmethyl]-urea are obtained in the form of a white solid.
(M.Pt.=176° C., Yield=94%).
Mass: 520. HPLC: 95.4%.
$^1$H NMR (CDCl$_3$, 400 Mz): 1.13 (s, 12H); 1.70 (m, 8H); 3.18-3.26 (m, 2H); 3.45 (s, 2H); 4.36 (s, 1H); 5.79 (s, 1H); 6.21 (s, 1H); 7.17-7.19 (d, 2H, J=7.7 Hz); 7.33-7.37 (m, 5H).

EXAMPLE 2

1-(2,6-diisopropylphenyl)-3-[1-(2-iodophenylamino)-cyclopentylmethyl]-urea, compound (I.2) with R=H, $R_1$=$R_2$=iPr; $R_3$=H; $R_4$ and R'$_4$ are linked together to form a cyclopentyl; $R_5$=o-I-Ph (I.2)

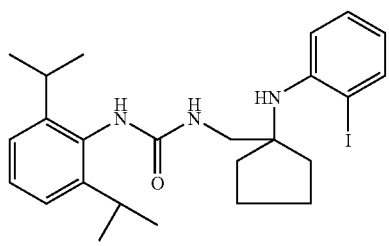

(a) Preparation of 1-(2-iodo-phenylamino)-cyclopentanecarbonitrile

Analogously to Example 1(a), by reaction of 3.5 g (16 mmol) of 2-iodo-aniline and 2 ml (15 mmol) of trimethylsilyl cyanide with 1.3 ml (14.7 mmol) of cyclopentanone, 4.3 g of 1-(2-iodophenylamino)cyclo-pentanecarbonitrile are obtained in the form of a brown oil. (Yield=98%).

(b) Preparation of 1-(2-iodo-phenylamino)-cyclopentanecarboxamide

Analogously to Example 1(b), by reaction of 4.5 g (14.4 mmol) of 1-(2-iodo-phenylamino)-cyclopentane-carbonitrile with 30 ml of concentrated sulfuric acid, 3.1 g of 1-(2-iodophenylamino)-cyclo-pentanecarboxamide are obtained in the form of a white paste. (Yield=65%).

(c) Preparation of (1-aminomethyl-cyclopentyl)-(2-iodo-phenyl)-amine

Analogously to Example 1(c), by reaction of 3 g (9.08 mmol) of 1-(2-iodophenylamino)-cyclopentane-carboxamide with 9.1 ml (18.2 mmol) of borane-dimethyl sulfide, 2.4 g of (1-aminomethylcyclopentyl)-(2-iodo-phenyl)-amine are obtained in the form of a colorless oil. (Yield=83%).

(d) Preparation of 1-(2,6-diisopropylphenyl)-3-[1-(2-iodophenylamino)-cyclopentylmethyl]-urea Analogously to Example 1(d), by reaction of 1.4 g (4.42 mmol) of (1-aminomethylcyclopentyl)-(2-iodo-phenyl)-amine with 1.1 ml (5.35 mmol) of 2,6-diiso-propylphenyl isocyanate, 1.4 g of 1-(2,6-diisopropyl-phenyl)-3-[1-(2-iodophenylamino)-cyclopentylmethyl]-urea are obtained in the form of a white solid.

(M.Pt.=185° C., Yield=61%).

Mass: 519. HPLC: 93.7%.

$^1$H NMR (CDCl$_3$, 400 Mz): 1.11 (s, 12H); 1.71-1.80 (m, 8H); 3.18-3.25 (m, 2H); 3.55 (s, 2H); 4.5 (s, 1H); 5.89 (s, 1H); 6.45 (s, 1H); 6.74 (s, 1H); 7.10-7.17 (m, 3H); 7.31-7.35 (m, 2H); 7.58-7.60 (d, 1H, J=7.51 Hz).

EXAMPLE 3

1-[1-(biphenyl-4-ylamino)-cyclopentylmethyl]-3-(2,6-diisopropylphenyl)-urea, compound (I.3) with R═H, R$_1$═R$_2$═iPr; R$_3$═H; R$_4$ and R'$_4$ are linked together to form a cyclopentyl; R$_5$=p-BiPh (I.3)

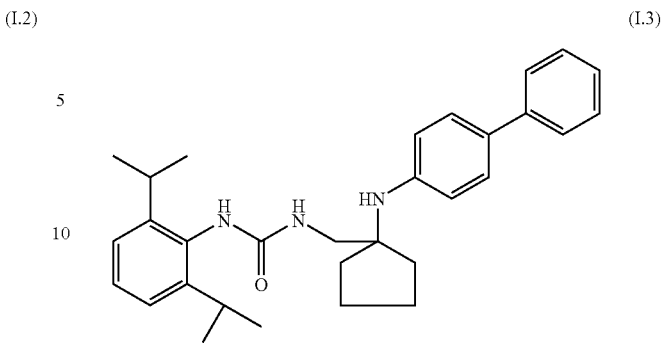

45 mg (0.37 mmol) of phenylboronic acid are added to 150 mg (0.29 mmol) of 1-(2,6-diisopropylphenyl)-3-[1-(4-iodophenylamino)-cyclopentylmethyl]-urea (Example 6d) in 20 ml of toluene. 370 µl (0.74 mmol) of a 2M aqueous solution of potassium carbonate are added. The reaction medium is degassed with nitrogen for 20 min, then 10 mg (8.65 µmol) of tetrakis-(triphenylphosphine)palladium are added. The medium is heated at 100° C. for 6 hours, then at ambient temperature for 10 days. It is then poured into water and extracted with ethyl acetate. The organic phases are combined and washed with water. They are dried over sodium sulfate. The solvents are evaporated and the residue is chromatographed on silica gel (heptane/ethyl acetate, 80/20 v/v). 78 mg of 1-[1-(biphenyl-4-ylamino)cyclopentylmethyl]-3-(2,6-diisopropyl-phenyl)-urea are obtained in the form of a white solid. (M.Pt.=198° C., Yield=57%).

Mass: 468. HPLC: 96.8%.

$^1$H NMR (CDCl$_3$, 400 Mz): 1.05 (s, 12H); 1.64-1.85 (m, 8H); 3.12-3.17 (m, 2H); 3.45 (s, 2H); 6.92-7.52 (m, 12H).

EXAMPLE 4

1-[1-(biphenyl-2-ylamino)-cyclopentylmethyl]-3-(2,6-diisopropyl-phenyl)-urea, compound (I.4) with R═H, R$_1$═R$_2$═iPr; R$_3$═H; R$_4$ and R'$_4$ are linked together to form a cyclopentyl; R$_5$=o-BiPh (I.4)

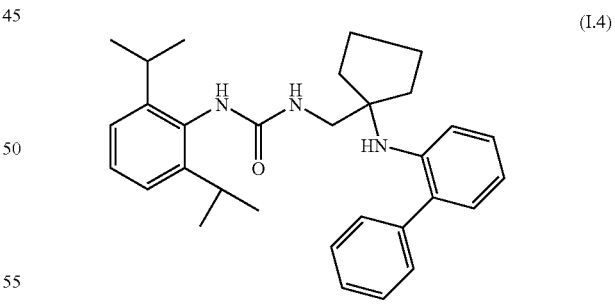

Analogously to Example 1, by reaction of 200 mg (0.38 mmol) of 1-(2,6-diisopropylphenyl)-3-[1-(2-iodo-phenylamino)-cyclopentylmethyl]-urea with 60 mg (0.49 mmol) of phenylboronic acid, 500 µl (1 mmol) of a 2M aqueous solution of potassium carbonate and 13 mg (11.2 µmol) of tetrakis (triphenylphosphine)palladium, 40 mg of 1-[1-(biphenyl-2-ylamino)cyclopentylmethyl]-3-(2,6-diisopropyl-phenyl)-urea are obtained in the form of a white solid (M.Pt.=150° C., Yield=22%).

Mass: 470. HPLC: 84.16%.

$^1$H NMR CDCl$_3$ 400 Mz): 1.13 (s, 12H); 1.62 (m, 8H); 3.17-3.19 (m, 2H); 3.56 (s, 2H); 4.54 (s, 1H); 5.67 (s, 1H); 6.73 (s, 1H); 6.97-7.54 (m, 12H).

EXAMPLE 5

Biological Tests

The compounds of formula (I) according to the invention were subjected to a test making it possible to evaluate their inhibitory activity towards the enzyme ACAT-1 inspired by the following publication: "Identification of ACAT1- and ACAT2-specific inhibitors using a novel, cell based fluorescence assay: individual ACAT uniqueness" J. lipid. Res (2004) vol 45, pages 378-386. The principle of this test is based on the use of NBD-cholesterol, an analogue of cholesterol whose fluorescence depends on its environment. When it is in a polar environment, it is weakly fluorescent, whereas in a non-polar environment it is strongly fluorescent. Free NBD-cholesterol localizes in the cell membranes and is weakly fluorescent in this polar environment. When the NBD-cholesterol is esterified by ACAT, the ester of NBD-cholesterol localizes in the non-polar lipid droplets and is then strongly fluorescent.

The following method is applied: the HepG2 cells are incubated in the presence of NBD-cholesterol (1 μg/ml) and of the compound of formula (I) to be tested in transparent-bottomed black 96-well plates at a level of 30000 cells per well. After incubation for 6 hrs at 37° C., under 5% CO$_2$, the medium is removed by inversion and the cells are washed twice with 100 μl of PBS. After addition of 50 μl of lysis buffer (10 mM NaPO$_4$, 1% lgepal), the plates are shaken for 5 mins and read in fluorescence (excitation 490 nm, emission 540 nm) on a FUSION instrument (Perkin Elmer). By way of illustration, an IC$_{50}$ of 24.1 nM is obtained for the compound (I.2) and an IC$_{50}$ of 9.5 nM is obtained for the compound (I.4).

EXAMPLE 6

Formulation Examples

Various specific formulations based on the compounds according to the invention are given below.

A—Oral Route:

| (a) 0.2 g Tablet: | |
| --- | --- |
| Compound (I.3) | 0.001 g |
| Starch | 0.114 g |
| Dicalcium phosphate | 0.020 g |
| Silica | 0.020 g |
| Lactose | 0.030 g |
| Talc | 0.010 g |
| Magnesium stearate | 0.005 g |
| (b) Drinkable suspension in 5 ml ampoules: | |
| Compound (I.1) | 0.001 g |
| Glycerine | 0.500 g |
| 70% sorbitol | 0.500 g |
| Sodium saccharinate | 0.010 g |
| Methyl parahydroxybenzoate | 0.040 g |
| Perfume | qs |
| Purified water | qsp 5 ml |

B—Topical Route:

| (a) Ointment: | |
| --- | --- |
| Compound (I.2) | 0.300 g |
| Codex white Vaseline | qs 100 g |
| (d) Lotion: | |
| Compound (I.4) | 0.100 g |
| Polyethylene glycol (PEG 400) | 69.900 g |
| 95% ethanol | 30.000 g |
| (e) Hydrophobic ointment: | |
| Compound (I.1) | 0.300 g |
| Isopropyl myristate | 36.400 g |
| Silicone oil("Rhodorsil 47 V 300") | 36.400 g |
| Beeswax | 13.600 g |
| Silicone oil ("Abil 300.000 cst") | qsp 100 g |
| (f) Non-ionic oil-in-water cream: | |
| Compound (I.2) | 1.000 g |
| Cetyl alcohol | 4.000 g |
| Glycerol monostearate | 2.500 g |
| PEG 50 stearate | 2.500 g |
| Shea butter | 9.200 g |
| Propylene glycol | 2.000 g |
| Methyl parahydroxybenzoate | 0.075 g |
| Propyl parahydroxybenzoate | 0.075 g |
| Sterile demineralized water | qsp 100 g |

Each patent, patent application, publication, text and literature article/report cited or indicated herein is hereby expressly incorporated by reference in its entirety.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A phenylurea compound having the following formula (I):

wherein,
R is a hydrogen atom, a (C$_1$-C$_6$) alkyl radical, a —CH$_2$—NR$_6$R$_7$ radical, a —C(O)—NR$_6$R$_7$ radical or a —C(S)—NR$_6$R$_7$ radical, wherein R$_6$ is a hydrogen atom or a (C$_1$-C$_4$) alkyl radical and R$_7$ is a hydrogen atom, a phenyl or a cycloalkyl radical,
R$_1$ is a hydrogen atom, a (C$_1$-C$_6$) alkyl radical or a chlorine, bromine or fluorine atom,
R$_2$ is a (C$_1$-C$_6$) alkyl radical,
R$_3$ is a hydrogen atom or a (C$_1$-C$_6$) alkyl radical,
R$_4$ and R'$_4$ are identical and are each a (C$_1$-C$_6$) alkyl radical or else R$_4$ and R'$_4$ are linked together and form, with the carbon atom from which they depend, a cycloalkyl group, an indanyl group, or a saturated heterocyclic group selected from the group consisting of piperidine, tetrahydropyran, pyrrolidine, tetrahydrothiophene, tetrahydrofuran and azetidine groups, wherein the piperidine, pyrrolidine and azetidine groups are optionally substituted on the nitrogen atom with an $R_8$, —C(O)$R_8$ or —SO$_2R_8$ radical, with $R_8$ being a ($C_1$-$C_4$) alkyl radical, and $R_5$ is a phenyl radical ortho, meta or para monosubstituted with an iodine atom or with a phenyl, 2-pyridyl, 3-pyridyl or 4-pyridyl radical; or a pharmaceutically acceptable salt thereof.

2. A phenylurea compound as defined by claim 1, wherein, in formula (I):
R is a hydrogen atom,
$R_1$ is a methyl, ethyl, isopropyl or t-butyl radical,
$R_2$ is a methyl, ethyl, isopropyl or t-butyl radical,
$R_3$ is a hydrogen atom,
$R_4$ and $R'_4$ are identical and are each an ethyl radical, or $R_4$ and $R'_4$ are linked together and form, with the carbon atom from which they depend, either a cyclopentyl, cyclohexyl, cycloheptyl, or indanyl radical, or a tetrahydropyran or piperidine group, or piperidine substituted on the nitrogen atom with an $R_6$, —C(O)$R_6$ or —SO$_2R_6$ radical, with $R_6$ being a ($C_1$-$C_4$) alkyl radical, and
$R_5$ is an o-, m- or p-biphenyl, o-, m- or p-iodophenyl, o-, m- or p-(2-pyridyl)phenyl, o-, m- or p-(3-pyridyl)phenyl or o-, m- or p-(4-pyridyl)phenyl radical.

3. A phenylurea compound as defined by claim 1, wherein, in formula (I), R is a hydrogen atom.

4. A phenylurea compound as defined by claim 1, wherein, in formula (I), $R_1$ is an ethyl, isopropyl or t-butyl radical.

5. A phenylurea compound as defined by claim 1, wherein, in formula (I), $R_2$ is a methyl, ethyl or isopropyl radical.

6. A phenylurea compound as defined by claim 1, wherein, in formula (I), $R_3$ is a hydrogen atom.

7. A phenylurea compound as defined by claim 1, wherein, in formula (I), $R_4$ and $R'_4$ are identical and are each an ethyl radical, or $R_4$ and $R'_4$ are linked together and form, with the carbon atom from which they depend, either a cyclopentyl or cyclohexyl group, or a tetrahydropyran or piperidine group, or piperidine substituted on the nitrogen atom with a methyl, ethyl, —C(O)CH$_3$ or —SO$_2$CH$_3$ radical.

8. A phenylurea compound as defined by claim 1, wherein, in formula (I), $R_5$ is an o- or p-biphenyl, o- or p-iodophenyl, o- or p-(2-pyridyl)phenyl, o- or p-(3-pyridyl)phenyl or o- or p-(4-pyridyl)phenyl radical.

9. A phenylurea compound as defined by claim 1, selected from the group consisting of:
1-(2,6-diisopropylphenyl)-3-[1-(4-iodophenylamino)-cyclopentylmethyl]urea,
1-(2,6-diisopropylphenyl)-3-[1-(2-iodophenylamino)-cyclopentylmethyl]urea,
1-[1-(biphenyl-4-ylamino)cyclopentylmethyl]-3-(2,6-diisopropylphenyl)urea,
1-[1-(biphenyl-2-ylamino)cyclopentylmethyl]-3-(2,6-diisopropylphenyl)urea,
1-[1-(biphenyl-2-ylamino)cyclopentylmethyl]-3-(2,6-diethylphenyl)urea,
1-[1-(biphenyl-2-ylamino)cyclohexylmethyl]-3-(2,6-diisopropylphenyl)urea,
1-[1-(biphenyl-2-ylamino)cyclopentylmethyl]-3-(2-tert-butyl-6-methylphenyl]urea,
1-(2,6-diisopropylphenyl)-3-[1-(2-pyridin-2-yl-phenylamino)cyclopentylmethyl]urea,
1-(2,6-diisopropylphenyl)-3-[1-(2-pyridin-4-yl-phenylamino)cyclopentylmethyl]urea,
1-(2,6-diisopropylphenyl)-3-[1-(2-pyridin-3-yl-phenylamino)cyclopentylmethyl]urea,
1-(2,6-diisopropylphenyl)-3-[1-(2-pyridin-4-yl-phenylamino)cyclohexylmethyl]urea,
1-(2,6-diisopropylphenyl)-3-[1-(2-pyridin-3-yl-phenylamino)cyclohexylmethyl]urea,
1-(2,6-diisopropylphenyl)-3-[1-(2-pyridin-2-yl-phenylamino)cyclohexylmethyl]urea,
1-(2,6-diisopropylphenyl)-3-[1-(4-pyridin-2-yl-phenylamino)cyclopentylmethyl]urea,
1-(2,6-diisopropylphenyl)-3-[1-(4-pyridin-4-yl-phenylamino)cyclopentylmethyl]urea,
1-(2,6-diisopropylphenyl)-3-[1-(4-pyridin-3-yl-phenylamino)cyclopentylmethyl]urea,
1-[4-(biphenyl-2-ylamino)piperidin-4-ylmethyl]-3-(2,6-diisopropylpheny)urea;
1-[4-(biphenyl-2-ylamino)-1-methylpiperidin-4-yl-methyl]-3-(2,6-diisopropylphenyl)urea,
1-[1-acetyl-4-(biphenyl-2-ylamino)piperidin-4-yl-methyl]-3-(2,6-diisopropylphenyl)urea,
1-[4-(biphenyl-2-ylamino)-1-methanesulfonyl-piperidin-4-ylmethyl]-3-(2,6-diisopropylphenyl)urea,
1-[4-(biphenyl-2-ylamino)-1-ethylpiperidin-4-yl-methyl]-3-(2,6-diisopropylphenyl)urea, and
1-[4-(biphenyl-2-ylamino)tetrahydropyran-4-yl-methyl]-3-(2,6-diisopropylpheny)urea;
and the pharmaceutically acceptable salts thereof.

10. A pharmaceutical composition comprising, formulated into a physiologically acceptable carrier, at least one phenylurea compound as defined by claim 1, or a pharmaceutically acceptable salt thereof.

11. A pharmaceutical composition as defined by claim 10, comprising a concentration of compound(s) of formula (I) ranging from 0.001 to 10% by weight relative to the total weight thereof.

12. A pharmaceutical composition as defined by claim 11, comprising a concentration of compound(s) of formula (I) ranging from 0.01 to 2% by weight relative to the total weight thereof.

13. A cosmetic composition comprising, formulated into a physiologically acceptable carrier, at least one phenylurea compound as defined by claim 1, or a physiologically acceptable salt thereof.

14. A cosmetic composition as defined by claim 13, comprising a concentration of compound(s) of formula (I) ranging from 0.001 to 3% by weight relative to the total weight thereof.

15. A pharmaceutical composition as defined by claim 10, formulated for topical application.

16. A pharmaceutical composition as defined by claim 15, comprising a cream, a milk, a lotion, a gel, an ointment, a pomade, suspensions of microspheres or nanospheres or lipid or polymeric vesicles, impregnated tampons, solutions, sprays, foams, sticks, soaps, shampoos or cleansing bases.

17. A cosmetic composition as defined by claim 13, formulated for body or hair hygiene.

18. A method for treatment of a disorder selected from the group consisting of hyperseborrhoea, acne, seborrhoeic dermatitis, atopic dermatitis, blepharitis, meibomitis, chalazion, dry eye, conjunctivitis, and keratoconjunctivitis, said method comprising administering to an individual in need of such treatment, for such period of time as required to elicit the desired result, a thus effective amount of at least one phenylurea compound as defined by claim 1, or a pharmaceutically acceptable salt thereof.

19. The method as defined by claim 18, wherein the disorder is acne.

20. A process for the preparation of a compound of formula (I) as defined by claim 1, which comprises the following steps:

reacting a primary or secondary amine of formula (1):

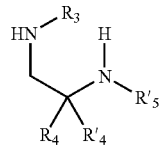

(1)

wherein R'$_5$ is the group R$_5$ or precursor thereof with a compound of formula (2):

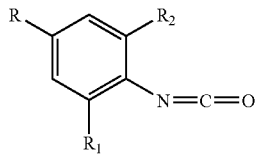

(2)

to obtain a compound of formula (I'):

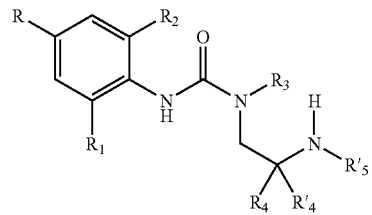

(I')

wherein R'$_5$ is the group R$_5$ or a precursor thereof and then, when R'$_5$ is different from R$_5$, transforming the group R'$_5$ to obtain the desired group R$_5$.

* * * * *